United States Patent [19]

Brunetti et al.

[11] Patent Number: 4,904,643
[45] Date of Patent: Feb. 27, 1990

[54] THYMUS DERIVATIVE ACTIVE AFTER ORAL ADMINISTRATION, METHODS OF PREPARATION AND PHARMACEUTICAL COMPOSITIONS

[75] Inventors: Brunetto Brunetti; Marco Prada, both of Milan, Italy

[73] Assignee: Ellem Industria Farmaceutica, s.r.l., Milan, Italy

[21] Appl. No.: 60,446

[22] Filed: Jun. 11, 1987

[30] Foreign Application Priority Data

Jul. 10, 1986 [IT] Italy ................................ 21097 A/86

[51] Int. Cl.[4] ...................... A61K 37/02; C07K 1/14; C07K 3/02; C07K 15/00
[52] U.S. Cl. ..................................... 514/21; 530/301; 530/344; 530/395; 530/399; 530/412; 530/837; 530/854
[58] Field of Search ............... 530/301, 344, 399, 854, 530/837, 412, 395; 514/21; 424/95

[56] References Cited

U.S. PATENT DOCUMENTS

| | | | |
|---|---|---|---|
| 4,077,949 | 3/1978 | Goldstein | 530/854 |
| 4,250,084 | 2/1981 | Trainin | 530/837 |
| 4,374,828 | 2/1983 | Folkers et al. | 530/837 |
| 4,377,511 | 3/1983 | Lopukhim et al. | 514/21 |
| 4,388,234 | 6/1983 | Horecker | 530/344 |
| 4,500,450 | 2/1985 | Seipke | 530/837 |
| 4,571,336 | 2/1986 | Houck et al. | 514/21 |

OTHER PUBLICATIONS

Lehminger, Biochemistry, 2nd edition, Worth publishers, Inc. (pp. 100–101, 225–226) 1975.

*Primary Examiner*—Delbert R. Phillips
*Assistant Examiner*—Christina Chan
*Attorney, Agent, or Firm*—Birch, Stewart, Kolasch & Birch

[57] ABSTRACT

Thymolymphotropin, a thymus derivative able to stimulate the differentiation and the function of T-lymphycytes, is active after oral administration and can be prepared through a process of partial acid lysis of mammal thymuses. Pharmaceutical compositions containing thymolymphotropin are utilized in the treatment of primary and secondary immunodeficiencies.

16 Claims, 5 Drawing Sheets

SCHEME OF TLT PROCESSING

HPLC PROFILE OF THYMOLYMPHOTROPIN

HPLC PROFILE OF FREE AMINO ACIDS CONTAINED IN TLT

SAMPLE AMOUNT : 1.0000
STANDARD AMOUNT : 1.0000

| PK NO | RETEN TIME | BC | PEAK NAME | MG/G | ACTUAL AREA | GP |
|---|---|---|---|---|---|---|
| 2 | 2.58 | 1 | ASPARTIC AC | 9.2666 | 4079 | 0 |
| 3 | 4.77 | 1 | GLUTAMIC AC | 24.0309 | 9940 | 0 |
| 5 | 10.00 | 1 | SERINE | 6.9279 | 3559 | 0 |
| 6 | 12.13 | 1 | HISTIDINE | 0.9632 | 242 | 0 |
| 7 | 16.70 | 1 | GLYCINE | 7.5585 | 4681 | 0 |
| 8 | 16.87 | 1 | THREONINE | 3.7942 | 1728 | 0 |
| 9 | 21.87 | 1 | ARGININE | 5.4771 | 2207 | 0 |
| 10 | 23.65 | 2 | ALANINE | 6.7539 | 4163 | 0 |
| 12 | 25.13 | 1 | INTERNAL STD | 0.5000 | 5660 | 99 |
| 13 | 26.60 | 1 | TYROSINE | 2.8552 | 913 | 0 |
| 16 | 34.67 | 2 | METHIONINE | 1.6222 | 694 | 0 |
| 17 | 35.37 | 5 | VALINE | 4.3111 | 2487 | 0 |
| 18 | 39.23 | 1 | PHENYLALANIN | 3.1490 | 1027 | 0 |
| 19 | 42.93 | 1 | ISOLEUCINE | 2.6236 | 1326 | 0 |
| 20 | 45.18 | 1 | LEUCINE | 6.1425 | 2640 | 0 |
| 23 | 56.85 | 1 | LYSINE | 7.6238 | 815 | 0 |

|  | TOTAL AREA | NO. OF PEAKS |
|---|---|---|
| WHOLE SAMPLE : | 50474 | 23 |
| NAMED PEAKS : | 46161 | 16 |
| UN-NAMED PEAKS : | 4312 | 7 |

HPLC PROFILE OF FREE PROLINE CONTAINED IN TLT

METHOD PARAMETER

METHOD: PROL.1  DANSYL AMINO ACIDS
PLOT : PROL.2

SAMPLE: PROLINE
INJECTION NUMBER: 01

RUN AT: 11:31 ON: 86-02-04  INTERFACE NO: 1B

| | |
|---|---|
| START TIME | 0.1 |
| END TIME | 65.0 |
| DETECTION THRESHOLD | 2.00 |
| MINIMUM PEAK WIDTH | 5.0 |
| AREA REJECT THRESHOLD | 100.0 |

INTERNAL STANDARD

| | |
|---|---|
| DILUTION FACTOR : | 1.0000 |
| SAMPLE AMOUNT : | 1.0000 |
| STANDARD AMOUNT : | 1.0000 |

| PK NO | RETEN TIME | B C | PEAK NAME | MG/G | ACTUAL AREA | G P |
|---|---|---|---|---|---|---|
| 16 | 24.63 | 5 | INTERNAL STD | 1.0000 | 28373 | 99 |
| 18 | 31.93 | 1 | PROLINE | 6.5998 | 16442 | 0 |

| | TOTAL AREA | NO. OF PEAKS |
|---|---|---|
| WHOLE SAMPLE : | 418316 | 16 |
| NAMED PEAKS : | 44814 | 2 |
| UN-NAMED PEAKS : | 373502 | 14 |

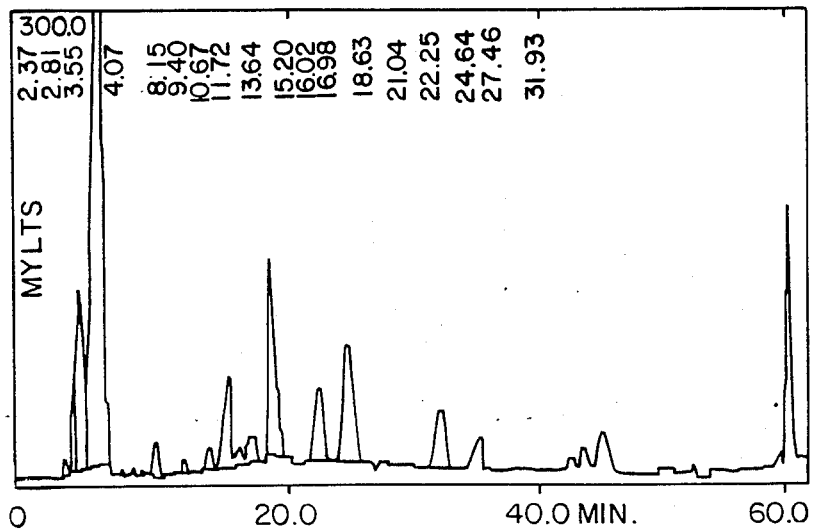

ISOELECTROFOCUSING OF THYMOLYMPHOTROPIN AT pH 3.5-10
COMPARISON BETWEEN DIFFERENT BATCHES.

BATCH     A    B    C    D

THYMUS DERIVATIVE ACTIVE AFTER ORAL ADMINISTRATION, METHODS OF PREPARATION AND PHARMACEUTICAL COMPOSITIONS

BACKGROUND AND SUMMARY OF THE INVENTION

The present invention refers to a thymus derivative, thymolyphotropin (TLT), able to stimulate the differentiation and function of T lymphocytes, characterized by the fact of being active also after oral administration.

The present invention refers also to a procedure for the isolation and purification of this derivative from mammal thymus.

It is known that some peptide derivatives active on T-lymphocytes, such as thymopoietin (U.S. Pat. No. 4,077,949), THF (Thymic Humoral Factor—U.S. Pat. No. 4,250,084) and thymosin (Zatz M. M. et al., Biol. Resp. Cancer 1: 219, 1982; Low T. L. K. and Goldstein A. L., Thymus 6: 27, 1984), have been obtained from thymus gland.

It is also known that all these derivatives have the disadvantage of being therapeutically efficacious only by parenteral route.

Therefore it would be very important to have a thymus derivative active also after oral administration, in order to overcome the many inconveniences related to the parenteral administration.

This requirement is fully satisfied by thymolymphotropin described in this invention; in fact this thymic derivative presents the characteristic (very important from the point of view of therapeutical use) of being active also after oral administration.

BRIEF DESCRIPTION OF THE DRAWINGS

FIGS. 4A and 4B shows the HPLC profile of free proline in the TLT of the invention.

DETAILED DESCRIPTION OF THE INVENTION

Thymolymphotropin, obtained through a process of partial acid lysis from mammal thymus, was shown to be useful in the treatment of secondary immunodeficiencies, such as physiological immunosenescence and immunodepression induced by antitumour treatments or infectious diseases.

According to the invention, TLT is obtained from mammal thymuses, more specifically from calf thymuses, through a process of partial acid lysis of the glands, in order to get mainly a content in low molecular weight (less than 10000 daltons) polypeptides. The process includes the elimination of proteins with molecular weight above 10000 daltons through four stages of elimination of the same at different isoelectric points and an ultrafiltration, before the elimination of the salts of the extract by means of an electrodialysis. The process is completed by concentrating the derivative by under vacuum thin layer evaporation and subsequent atomization, in order to obtain the final dry TLT.

Figure 1:
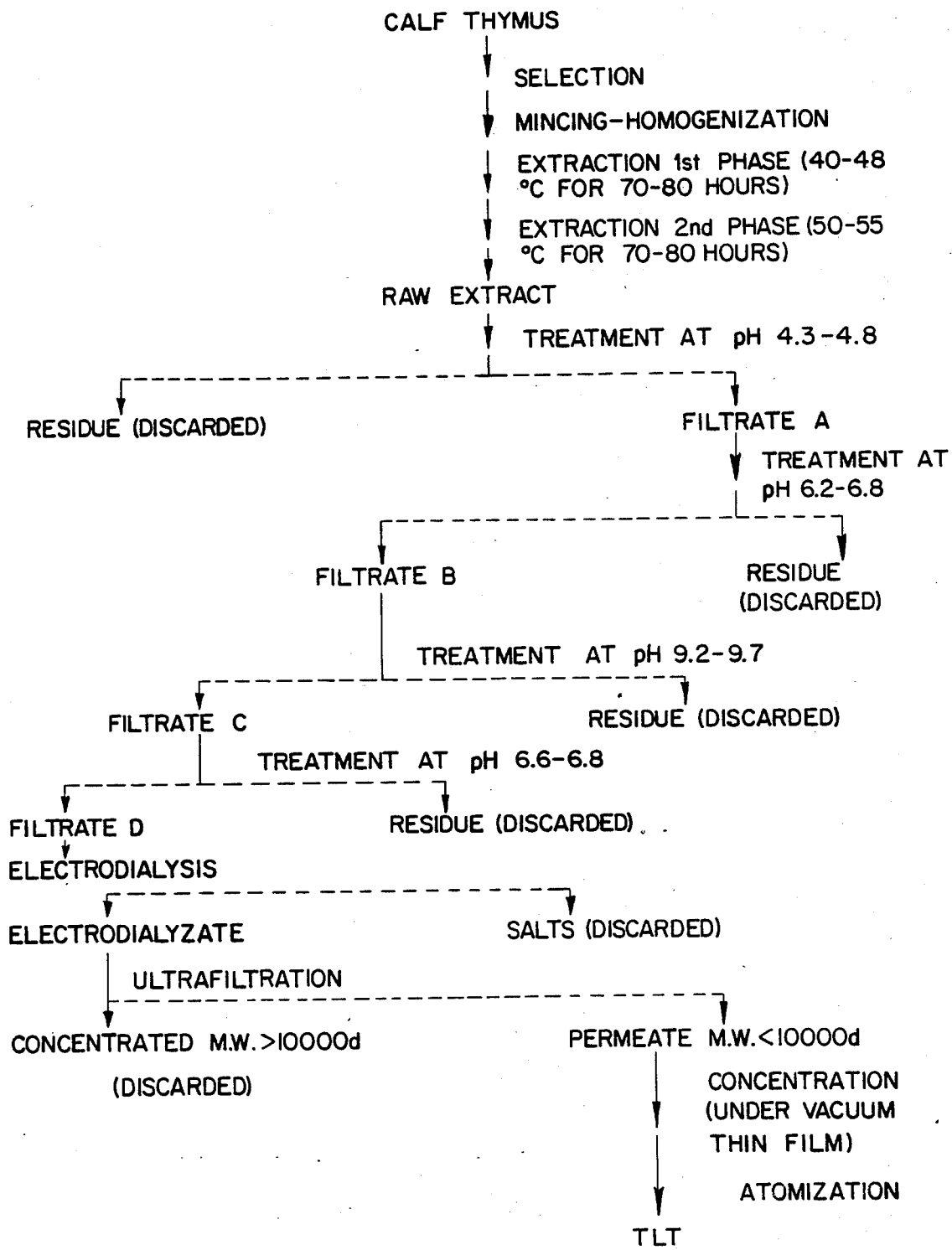
FIG. 1 represents a schematic flowchart of the process according to the invention.

The process of the invention can be schematized as shown in FIG. 1.

EXAMPLE OF PROCESS

Here a non-limitative example of the process according to the invention is shown.

1. Calf thymuses not yet physiologically involuted, in a state of activity thus devoid of evident fat infiltrations, are employed. The organ is minced in fragments with a diameter of about 2 mm and is mixed with 8-12% of an inorganic acid, particularly hydrochloric acid having a specific weight between 1.090 and 1.096. The mass is kept at room temperature (20-24 C.) for 18-24 hours.

2. After this period of time, the mass temperature is raised to 40-48 C. and so maintained for 70-80 hours, mixing for 30 min. at 5-10 hour intervals.

3. Next the temperature is raised to 50-55 C. for 70-80 hours mixing the mass for 30 min. at 5-10 hour intervals.

4. The product under process is subsequently treated, under stirring, with an aqueous solution of sodium hydroxide 1-2 N, until pH 4.3-4.8 is reached. The temperature is raised to 75-85 C. for 30 min. Then a filtration is performed with filter press (SEITZ SUPRA: SEITZ FILTER, WERKE, Bad Kreuznach, FGR). The filtrate is then brought to a low temperature (between 0 and +2 C.) and maintained at this temperature for 12-18 hours.

Next a further filtration is carried out with filter press and SEITZ SUPRA filters.

5. The filtrate is brought to the temperature of 20-25 C. and, under stirring, 1-2N sodium hydroxide is added until pH 6.2-6.8 is reached. The temperature is raised to 75-85 C. and, after 30 min., lowered to 20-25 C. then a filtration is performed with filter press and SEITZ SUPRA filters. The filtrate, cooled at 0/+2 C., is maintained at such temperature for 12-18 hours and subsequently a filtration is carried out with filter press and SEITZ SUPRA filters.

6. The filtrate, heated at 20-25 C., is treated under stirring with 1-2N sodium hydroxide until pH 9.2-9.7 is reached. Next the temperature is raised to 75-85 C. and, after 30 min., lowered to 20-25 C. A filtration is performed with filter press and SEITZ SUPRA filters. The obtained filtrate is cooled to 0/+2 C. and, 12-18 hours later, filtered with filter press and SEITZ SUPRA filters.

7. The filtrate is then treated, after heating at 20°-25 C., with 1-2N hydrochloric acid under stirring, until pH 6.6-6.8 is reached, then the temperature is raised to 75-85 C. for 20-40 min. Next it is cooled to 20-25 C. and a filtration is carried out with filter press and SEITZ SUPRA filters. The filtrate so obtained is cooled at 0/+2 C. and then is kept at such temperature for 72 hours.

8. After this lapse, a filtration is carried out on Millipore cartridge (Millipore Co., Bedford, Mass., USA).

9. The liquid obtained undergoes ultrafiltration with PTGC Millipore membranes (Millipore Co., Bedford, Mass., USA).

10. The liquid obtained undergoes electrodialysis with MEMBRANE apparatus (Milan, Italy) and polyethylene membranes loaded with anionic and cationic resin.

11. The effluent, containing substances with a molecular weight lower than 10000 daltons, is concentrated by evaporation (under vacuum thin layer evaporation concentrator—LUWA AG, Zurich, Switzerland) until the solution contains 13–16% of dry residue.

12. The drying of the concentrated solution is performed by means of a spray dryer supplied by NIRO ATOMIZER (Copenhagen, Denmark).

PROPERTIES OF TLT

The TLT so obtained presents the following characteristics:

I: CHEMICAL CHARACTERISTICS

1. HPLC map

Figure 2:
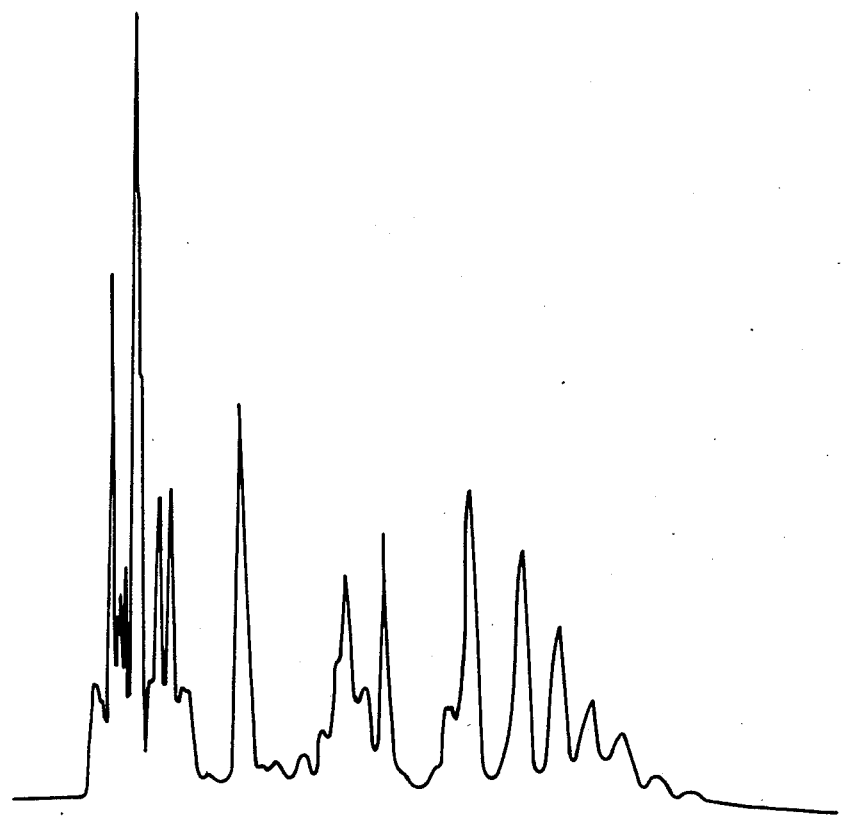
FIG. 2 shows the HPLC map of the TLT of the invention.

HPLC determination is performed on Reversed Phase C18 column at a wavelength of 280 nm (FIG. 2).

2. Peptides

The quantitative determination of peptides is performed by using the biuret reaction, evaluating at the spectrophotomer the colourings obtained at the wavelength of 546 nm. The mean peptide content of TLT is 487.9 mg/g on the dried basis (Coefficient of variation 9.8%—Table 1).

3. Total nitrogen

Total nitrogen is determined by the Kjeldahl's method; the mean value is 139.7 mg/g on the dried basis (Coefficient of variation 8.4%—Table 1).

4. Alpha-amino nitrogen

The alpha-amino nitrogen is determined by means of an acidimetric titration after reaction with formic acid; the mean value is 28.2 mg/g on the dried basis (Coefficient of variation 8.4%—Table 1).

5. Free amino acids

For the quali-quantitative determination of free amino acids, a reference standard mixture of twenty different amino acids undergoes pre-column derivativization by reaction with ortho-phtaladehyde or dansyl chloride.

Figures 3A, 3B:
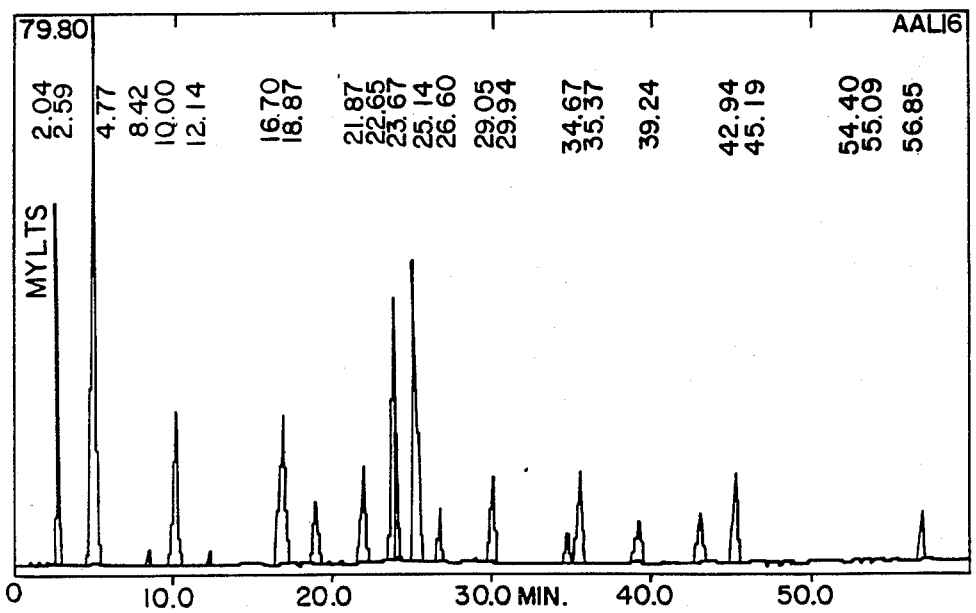
FIGS. 3A and 3B shows the HPLC profile of the free amino acids in the TLT of the invention.

By means of the same procedure the TLT sample under control undergoes derivatization. The following amino acids are evidenced by HPLC, with reversed phase column (C18), by means of a fluorimetric detector interfaced to an integrator: aspartic acid, glutamic acid, serine, histidine, glycine, threonine, alanine, arginine, tyrosine, methionine, valine, phenylalanine, isoleucine, leucine, lysine, proline (FIGS. 3 and 4). The mean total content in free amino acids is 90.9 mg/g on the dried basis (Coefficient of variation 15.2%—Table 1).

6. Nucleobases

The nucleobases are determined by HPLC with reversed phase column (C18) at a wavelength of 260 nm; the mean value is 34.7 mg/g on the dried basis (Coefficient of variation 30.1%—Table 1).

7. Carbohydrates (pentose+hexose)

Carbohydrates are determined by means of the anthrone reaction, reading the coloured product at the spectrophotometer at the wavelength of 625 nm and using ribose as standard reference. The mean value is 83.9 mg/g on the dried basis (Coefficient of variation 14.3%—Table 1).

II: ELECTROPHORETIC CHARACTERISTICS

Figure 5:
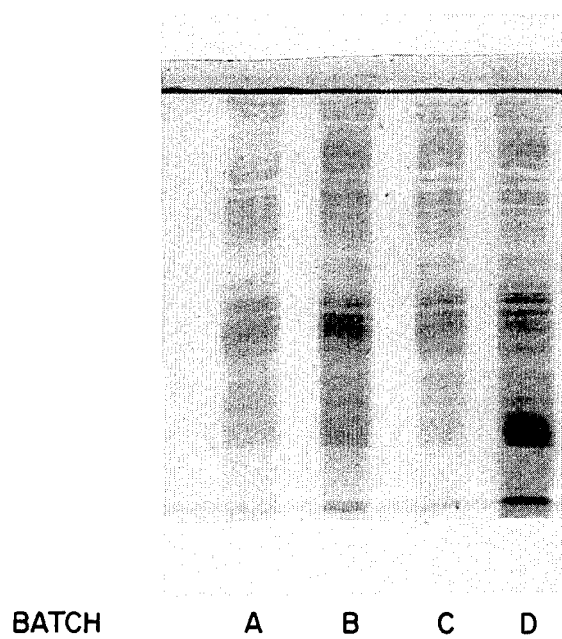
FIG. 5 shows the electrophoretic profile of the TLT.

The electrophoretic profile of TLT was obtained with isoelectrofocusing according to the following operating conditions: polyacrylamide gel:acrylamide 7%, ratio bisacrylamide:acrylamide 1:25, urea 8M, ampholine (LKB) 2%; focusing at 10 W constant for 4 hours; voltage: 1000 volts at equilibrium; staining was performed with $AgNO_3$; 200 mcg of TLT were loaded for each batch. The electrophoretic profile evidences the presence of some peptide fractions at both acid and basic pH (FIG. 5).

III: TOXICOLOGICAL CHARACTERISTICS

Acute toxicity studies have shown the total lack of toxicity of TLT; both in mice and rats, the oral and intraperitoneal LD50 exceed 5 g/kg.

IV: IMMUNOLOGICAL PROPERTIES

TLT has shown the following properties:
1. Differentiation of T lymphocytes

In vitro, TLT stimulates the differentiation of T lymphocytes, as it is able to induce the appearance of Thy 1.2 antigen, marker of T cells, on immature (pre-T) lymphocytes from the spleen of congenitally athymic and normal mice.

| TLT concentration (mcg/ml) | % Thy 1.2+ cells | |
|---|---|---|
| | Athymic nude mice | |
| — | 13+/−1.3 | 12+/−0.5 |
| 3.12 | 13+/−1.8 | 11.7+/−1.0 |
| 6.25 | 19+/−1.0 | 14+/−0.8 |
| 12.5 | 25+/−1.8 | 17+/−1.1 |
| 25 | 32+/−1.4 | 21+/−0.7 |
| 50 | 37+/−1.4 | 34+/−1.0 |
| 125 | 48+/−2.1 | 44+/−1.6 |
| 250 | 35+/−2.5 | 53+/−2.6 |
| 500 | 32+/−2.1 | 38+/−1.0 |
| | Normal mice | |
| — | 29 | |
| 31 | 31 | |
| 62.5 | 35 | |
| 125 | 41 | |
| 250 | 37 | |

2. In vitro modulation of TdT expression

TLT induces the maturation of thymocytes in vitro, as shown by the decrease in TdT+ cells.

| TLT conc. (mcg/ml) | % TdT+ thymocytes | |
|---|---|---|
| | BALB/c mice | C57BL/j mice |
| — | 55+/−1.4 | 64+/−2.1 |
| 25 | 44+/−1.4 | 39+/−1.4 |
| 50 | 37+/−1.8 | 35+/−1.0 |
| 125 | 30+/−2.5 | 41+/−1.1 |
| 250 | 32+/−3.2 | 44+/−1.8 |
| 500 | 30+/−1.4 | 42+/−2.1 |

3. In vitro stimulation of lymphokine production

TLT at the concentration of 100 mcg/ml stimulates in vitro in presence of phytohemoagglutinin (PHA) the production of IL-2 and BCGF by human peripheral blood lymphocytes (PBL); the presence of the lymphokines in the PBL supernatant is assessed through the evaluation of the mitogenic activity of PBL supernatants on T and B lymphocytes, determined as the incorporation of labelled thymidine.

| | Incorporation of thymidine (c.p.m.) | |
|---|---|---|
| Incubation with | T LYMPHOCYTES | B LYMPHOCYTES |
| PBL supernatant supernat. of | 284 | 172 |
| PBL + PHA supernat. of | 1438 | 1853 |
| PBL + PHA + TLT | 13864 | 11389 |
| supernat. of PBL + TLT | 349 | 586 |

-continued

| Incubation with | Incorporation of thymidine (c.p.m.) | |
|---|---|---|
| | T LYMPHOCYTES | B LYMPHOCYTES |
| PHA | 276 | 385 |
| TLT | 259 | 481 |

4. Restoration of circulating thymic hormone activity

The oral or intraperitoneal administration of TLT to 3 month old, congenitally athymic (nude) mice restores efficaciously the activity of the circulating thymic hormone, evaluated by the test of Thy 1.2 antigen induction on pre-T lymphocytes by the serum collected one hour after treatment.

| TLT (mg/mouse) route of administration | | % Thy 1.2+ cells induced by the serum taken at the following hours after the administration: | | | |
|---|---|---|---|---|---|
| | | 0.5 | 1 | 2 | 3 |
| — | | 4 | 3.5 | 4 | 4 |
| 0.62 | p.o. | 9 | 14 | 12 | 10 |
| 1.25 | p.o. | 16 | 18 | 16 | 11 |
| 3 | p.o. | 22 | 29 | 21 | 22 |
| 0.62 | i.p. | 24 | 36 | 32 | 30 |

In normal adult mice the circulating thymic hormone activity, evaluated with the test or rosette inhibition by azathioprine, totally disappears 10 days after thymectomy. The oral administration of TLT restores normal levels of thymic hormone activity, expressed as the maximum dilution still able to induce sensitivity to azathioprine in 50% of rosette-forming cells.

| Days after thymectomy | Plasma thymic hormone activity (1/log2) |
|---|---|
| 0 | 5.6 |
| 2 | 4 |
| 4 | 2 |
| 6 | 1 |
| 9 | not detectable |
| 12 (TLT administration) | not detectable |
| Hours after TLT administr. | |
| 4 | 3 |
| 8 | 4 |
| 12 | 4 |
| 24 | 2 |
| 36 | 1.6 |

5. Enhancement of the antibody response in immunodepressed or senescent animals

The treatment with TLT at the daily dose of 1.5 mg/mouse during the whole experimentation, by subcutaneous route, restores the secondary antibody response in mice immunized with sheep erythrocytes (SRBC) on days 0 and 21 and immunodepressed with cyclophosphamide injected on days 2–4. In senescent (24 month old) mice the i.p. administration of TLT at the dose of 0.625 mg/mouse every day from 10 days before the immunization until 10 days after, next every other day until day 28, determines a marked recovery of the antibody response.

V. THERAPEUTICAL EFFICACY

From the therapeutical point of view, TLT can be used in the whole wide field of primary and secondary immunodeficiencies, in particular in secondary immunodeficiencies in neoplastic patients, or in those induced in these subjects by chemo-radiotherapy, in infectious diseases with viral or bacterial aetiology, and in other fields where physiological characteristics result to be deviated in an involutive way, such as in aging.

1. Immunostimulation in neoplastic patients receiving chemoradiotherapy

In a double-blind trial, TLT, administered by intramuscular route at the dose of 12.5 mg/day for 1 month, then every other day for 3 months, at last twice a week for 3 more months in patients treated with antitumor chemotherapy and showing an initial immunodepression due to previous radio-chemotherapies, has increased the response to skin tests in 66% of patients in comparison with 42% in controls.

2. Restoration of the immune function in elderly people

After acute oral administration as capsules, TLT at the dose of 50–500 mg has determined the appearance in serum of over 75 year old subjects of a FTS (Facteur Thymique Sérique-like activity, evaluated with the test of rosette inhibition.

After i.m. adminstration of TLT at the daily dose of 12.5 mg for 20 days in 65–75 year old subjects, 87% of cases has shown a positive response to at least one of 5 different intradermic recall tests, in comparison with 45% in the control group.

3. Chicken-pox

The treatment with 37.5 mg/day of TLT as oral solution in 10 children aged 3–11 years has reduced the duration of the fever and of the vescicular phase, as well as the number of bacterial complications, in comparison with controls in 3/10 of whom complications (bronchopneumonia) were observed, versus none in the treated group.

4. Acute viral hepatitis

TLT was administered for 30 days as oral solution at the daily dose of 75 mg in patients with acute type B viral hepatitis in a double blind clinical trial. At the end of treatment SGOT and SGPT decreased in comparison with controls, HBsAg became negative in 67% of cases compared with 53% in the controls, total T lymphocytes and OKT4+ (helper) lymphocytes remained unchanged, while OKT8+ (suppressor) lymphocytes significantly decreased. The OKT4/OKT8 ratio increased significantly in treated patients from 1.28 to 1.66, while it slightly decreased in controls (from 1.55 to 1.45).

EXAMPLES OF PHARMACEUTICAL FORMS

TLT can be used as a drug, for example, in a pharmaceutical composition containing it in association with a compatible carrier such as sterile water or physiological solution for parenternal administration (ampoules or lyophilized ampoules for parenteral use) and distilled water or ethylcellulose for oral administration (respectively for drops or oral solution and for gelatine capsules).

Pharmaceutical compositions can be subject to conventional pharmaceutical operations such as sterilization and contain conventional additives such as preservatives, stabilizers, humidifiers etc.

Pharmaceutical compositions are prepared according to wellknown methods.

Here some examples of pharmaceutical formulations are shown.

Example 1: Lyophilized ampoules with solvent ampoules, for intramuscular use, each containing 7–14 mg of TLT; mannitol and/or lactose and/or aminoacetic acid can be used as carriers.

Example 2: Vials for oral use. Ten ml of solution containing 35–70 mg of TLT together with a sweetener (sorbitol or sucrose or saccharin). The pH ranges between 4 and 6 and can be opportunely adjusted with citric acid.

Example 3: Capsules in gelatin containing 70 mg of TLT; precipitated silica and microcrystalline cellulose are used as carriers.

Example 4: Solution for administration as drops, containing 28 mg/ml of TLT and a preservative (p-hydroxybenzoates or sodium benzoate).

Example 5: Cream for topical use containing TLT 2% plus water, glycerol, hydrophilic or lipophilic emulsifying agents, consistency factors as carriers, hydrophilic or lipophilic preservatives, and possibly parfum.

TABLE 1

| BATCH | PEPTIDES mg/g | TOTAL NITROGEN mg/g | TLT ALPHA-AMINO NITROGEN mg/g | FREE-AMINO ACIDS mg/g | NUCLEOBASES mg/g | CARBO TES AS mg/g |
|---|---|---|---|---|---|---|
| 184 | 545 | 145 | 27,0 | 100,4 | 25,0 | 10 |
| 1585 | 507 | 123 | 26,7 | 70,1 | 46,7 | 67 |
| 1184 | 519 | 148 | 27,0 | 107 | 22,9 | 10 |
| 1685 | 402 | 128 | 28,7 | 104 | 45,2 | 76 |
| 3084 | 485 | 151 | 31,9 | 95,1 | 31,6 | 79 |
| 2083 | 533 | 159 | 30,6 | 106 | 27,5 | 74 |
| 584 | 508 | 141 | 26,7 | 82,6 | 27,6 | 77 |
| 1385 | 439 | 138 | 30,5 | 81,0 | 50,9 | 76 |
| 884 | 510 | 139 | 28,6 | 90,2 | 26,4 | 90 |
| 1785 | 431 | 125 | 24,0 | 72,2 | 42,6 | 95 |
| Average | 487,9 | 139,7 | 28,2 | 90,9 | 34,7 | 83 |
| Coefficient of variation | 9,8% | 8,4% | 8,4% | 15,2% | 30,1% | 14 |

All the data are calculated on the dried basis

We claim:

1. A process for preparing a thymus derivative including the following steps:
   (a) subjecting thymus tissue to a first treatment with an inorganic acid at about room temperature for 18 to 24 hours;
   (b) increasing the temperature of the product under process to values ranging from 40° to 48° C. and maintaining said temperature for about 70–80 hours;
   (c) subsequently increasing the temperature of the product to values ranging from 50° to 55° C. and maintaining said temperature for 70 to 80 hours;
   (d) raising the pH of the obtained solution to values ranging from 4.3 to 4.8 and maintaining the solution at 75° to 85° C. for 30 minutes;
   (e) filtering the solution to produce a first filtrate;
   (f) adjusting the pH of said first filtrate to values ranging from 6.2 to 6.8;
   (g) filtering said first filtrate to produce a second filtrate;
   (h) adjusting the pH of said second filtrate to values ranging from 9.2 to 9.7;
   (i) filtering said second filtrate to produce a third filtrate;
   (j) adjusting the pH of said third filtrate to values ranging from 6.6 to 6.8;
   (k) removing high molecular weight proteins from said third filtrate to produce a fourth filtrate having a protein content consisting essentially of proteins with a molecular weight of less than 10,000 daltons; and
   (l) removing salts from said fourth filtrate.

2. A process according to claim 1, wherein said high molecular weight proteins are removed by subjecting said third filtrate to filtration and ultrafiltration.

3. A process according to claim 1 wherein the inorganic acid employed in said first treatment of the thymus is hydrochloric acid.

4. A process according to claim 1, wherein said first filtrate is maintained at pH 6.2 to 6.8 for about 12 to 18.5 hours.

5. A process according to claim 1, wherein said second filtrate is maintained at pH 9.2 to 9.7 for at least about 30 minutes.

6. A process according to claim 1, wherein said third filtrate is maintained at pH 6.6 to 6.8 for at least about 20 minutes.

7. A process according to claim 1, wherein said first filtrate is maintained at pH 6.2 to 6.8 at a temperature of 75° to 85° C. for about 30 minutes.

8. A process according to claim 1 wherein said second filtrate is maintained at pH 9.2 to 9.7 at a temperature of 75° to 85° C. for about 30 minutes.

9. A process according to claim 1 wherein said third filtrate is maintained at pH 6.6 to 6.8 at a temperature of 75° to 85° C. for about 20 to 40 minutes.

10. A process according to claim 1, wherein said fourth filtrate is maintained at 0°–2° C. for about 72 hours.

11. A process according to claim 1 wherein said thymus tissue is calf thymus.

12. A thymus derivative produced according to the process described in claim 1.

13. A pharmaceutical composition containing an effective T-lymphocyte-stimulating amount of thymus derivative obtained according to claim 12, together with a pharmaceutically acceptable carrier or diluent.

14. A pharmaceutical composition according to claim 13 in a form suitable for oral administration.

15. A pharmaceutical composition according to claim 13 in a form suitable for parenteral administration.

16. A pharmaceutical composition according to claim 13, in a for suitable for topical administration.

* * * * *